United States Patent [19]
Lemire et al.

[11] Patent Number: 5,974,787
[45] Date of Patent: Nov. 2, 1999

[54] METHOD FOR TESTING THE FUNCTIONAL CAPABILITY OF A CATALYTIC CONVERTER WITH AN OXYGEN SENSOR

[75] Inventors: Bertrand Lemire, Regensburg; Willibald Schürz, Aufhausen, both of Germany

[73] Assignee: Siemens Aktiengesellschaft, Munich, Germany

[21] Appl. No.: 08/884,773

[22] Filed: Jun. 30, 1997

Related U.S. Application Data

[63] Continuation of application No. PCT/DE96/01922, Oct. 8, 1996.

[30] Foreign Application Priority Data

Oct. 31, 1995 [DE] Germany .......................... 195 40 673

[51] Int. Cl.$^6$ ...................................................... F01N 3/00
[52] U.S. Cl. ............................... 60/274; 60/277; 73/118.1
[58] Field of Search ........................... 60/274, 276, 277; 73/118.1

[56] References Cited

U.S. PATENT DOCUMENTS

| | | | |
|---|---|---|---|
| 4,617,795 | 10/1986 | Abthoff et al. | |
| 4,884,066 | 11/1989 | Miyata et al. | 73/118.1 |
| 5,357,750 | 10/1994 | Ito et al. | |
| 5,426,934 | 6/1995 | Hunt et al. | 60/277 |

FOREIGN PATENT DOCUMENTS

| | | |
|---|---|---|
| 0 743 431 A2 | 11/1996 | European Pat. Off. . |
| 3024449 A1 | 1/1982 | Germany . |
| 3830515 A1 | 3/1990 | Germany . |
| 40 19 572 A1 | 1/1992 | Germany . |
| 40 22 546 A1 | 1/1992 | Germany . |
| 4320881 A1 | 9/1994 | Germany . |
| 93/03358 | 2/1993 | WIPO . |

OTHER PUBLICATIONS

Publication by Roth–Technik GmbH, Gaggenau "Double Function of a Probe".

P.G. Eastwood et al, "A new method for on–vehicle detection of catalyst malfunction based upon measurement of non–equilibrated gas mixtures", Sensors and Actuators B 24–25 (1995), pp. 665–669.

Peter Eastwood et al., "Konzept zur Überprüfung der Funktionstauglichkeit des Abgaskatalysators", Automobiltechnische Zeitschrift 96 (1994), pp. 18–24, method for detecting the functionality of a exhaust gas catalytic converter.

Primary Examiner—Thomas E. Denion
Attorney, Agent, or Firm—Herbert L. Lerner; Laurence A. Greenberg

[57] ABSTRACT

A method for testing the functional capability of a catalytic converter of an internal combustion engine uses an exhaust-gas probe having a measuring electrode for measuring the resistance of a metal oxide layer having low catalytic activity. The resistance of the metal oxide layer is dependent on the oxygen partial pressure in the exhaust gas, for a predetermined air factor. The conversion rate of a catalytic converter has an effect on the oxygen partial pressure in the exhaust gas downstream of the catalytic converter, so that the resistance of the metal oxide layer depends on the conversion efficiency of the catalytic converter. It is thus possible to test the functional capability of the catalytic converter with the simply constructed exhaust-gas probe using a simple resistance measurement.

8 Claims, 2 Drawing Sheets

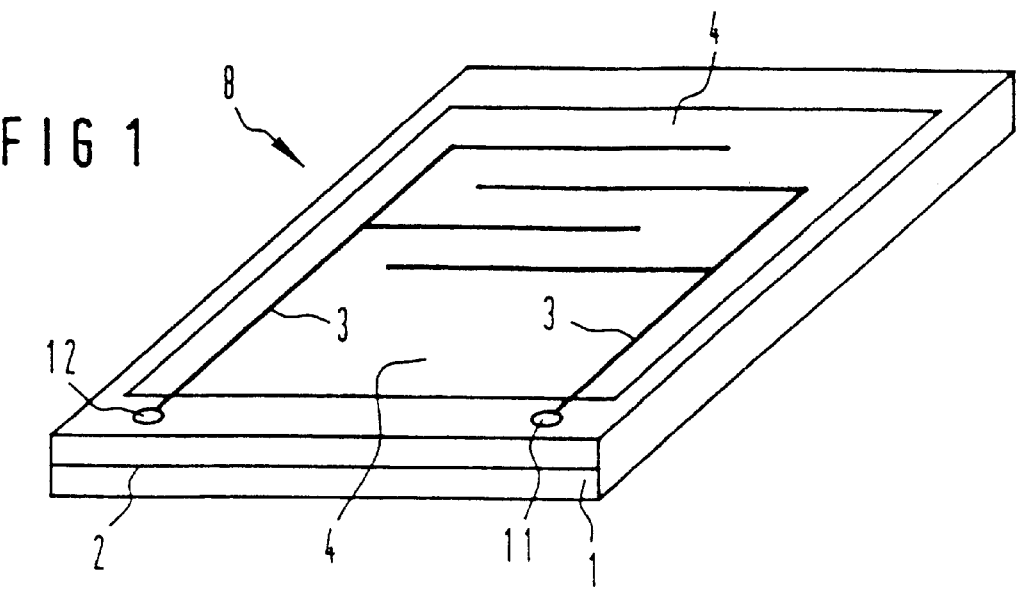
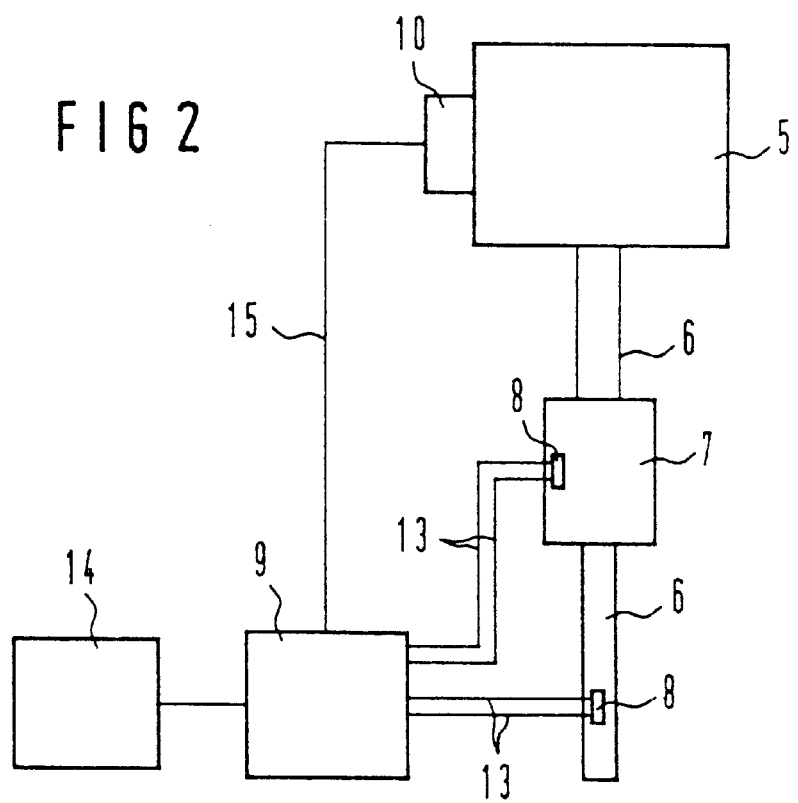

METHOD FOR TESTING THE FUNCTIONAL CAPABILITY OF A CATALYTIC CONVERTER WITH AN OXYGEN SENSOR

CROSS-REFERENCE TO RELATED APPLICATION

This application is a Continuation of International Application Serial No. PCT/DE96/01922, filed Oct. 8, 1996.

BACKGROUND OF THE INVENTION

FIELD OF THE INVENTION

The invention relates to a method for testing the functional capability of a catalytic converter of an internal combustion engine with an oxygen sensor which is disposed in a catalytic converter or in an exhaust pipe downstream of the catalytic converter, the oxygen sensor having a layer which has little or no catalytic effect on the exhaust gas.

Published International Patent Application WO 93/03358, corresponding to U.S. application Ser. No. 07/741,881, filed Aug. 7, 1991, has already disclosed a method for testing a catalytic converter with an oxygen sensor. In that case, a first oxygen sensor having high catalytic activity, and a second oxygen sensor having low catalytic activity, are disposed downstream of the catalytic converter. In order to assess the functional capability of the catalytic converter, shifts in output signals of the first and second oxygen sensors in relation to an exhaust-gas ratio of air to fuel are compared with one another. The oxygen sensors are based on oxygen-conducting zirconium oxide ($ZrO_2$). The evaluation method which is used is relatively elaborate.

SUMMARY OF THE INVENTION

It is accordingly an object of the invention to provide a method for testing the functional capability of a catalytic converter with an oxygen sensor, which overcomes the hereinafore-mentioned disadvantages of the heretofore-known methods of this general type and which is simple.

With the foregoing and other objects in view there is provided, in accordance with the invention, a method for testing the functional capability of a catalytic converter of an internal combustion engine, which comprises placing an oxygen sensor in a catalytic converter or in an exhaust pipe downstream of the catalytic converter; providing the oxygen sensor with a layer having at most little catalytic effect on exhaust gas; measuring resistance of the layer; comparing the measured resistance with a reference value to reach a result; and evaluating the result of the comparison as a measure of a conversion efficiency of the catalytic converter.

A particularly simple way of determining the functional capability of catalytic converters is by using an oxygen sensor which has minimal catalytic effect on the exhaust gas and has a resistance that depends on the oxygen partial pressure in the exhaust gas. The oxygen partial pressure in the exhaust gas is in turn a measure of the conversion efficiency of the catalytic converter.

In accordance with another mode of the invention, there is provided a method which comprises using values or characteristic curves for the resistance of the layer as a function of an air factor and of a conversion rate of the catalytic converter as the reference value, and determining the conversion rate of the catalytic converter from the comparison.

In accordance with a further mode of the invention, there is provided a method which comprises measuring the resistance of the layer for an air factor of less than one and for an air-fuel ratio of greater than one to determine a difference, and using the difference between the measured resistances as a measure of the conversion efficiency of the catalytic converter.

In accordance with an added mode of the invention, there is provided a method which comprises deciding that the catalytic converter is defective if the difference between the resistance values is greater than a limit value.

In accordance with a concomitant mode of the invention, there is provided a method which comprises forming the layer as a metal oxide layer.

Other features which are considered as characteristic for the invention are set forth in the appended claims.

Although the invention is illustrated and described herein as embodied in a method for testing the functional capability of a catalytic converter with an oxygen sensor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a diagrammatic, perspective view of an exhaust-gas probe;

FIG. 2 is a block diagram of a configuration for investigating the functional capability of a catalytic converter;

DESCRIPTION OF THE PREFERRED EMBODIMENTS

Figure 3:
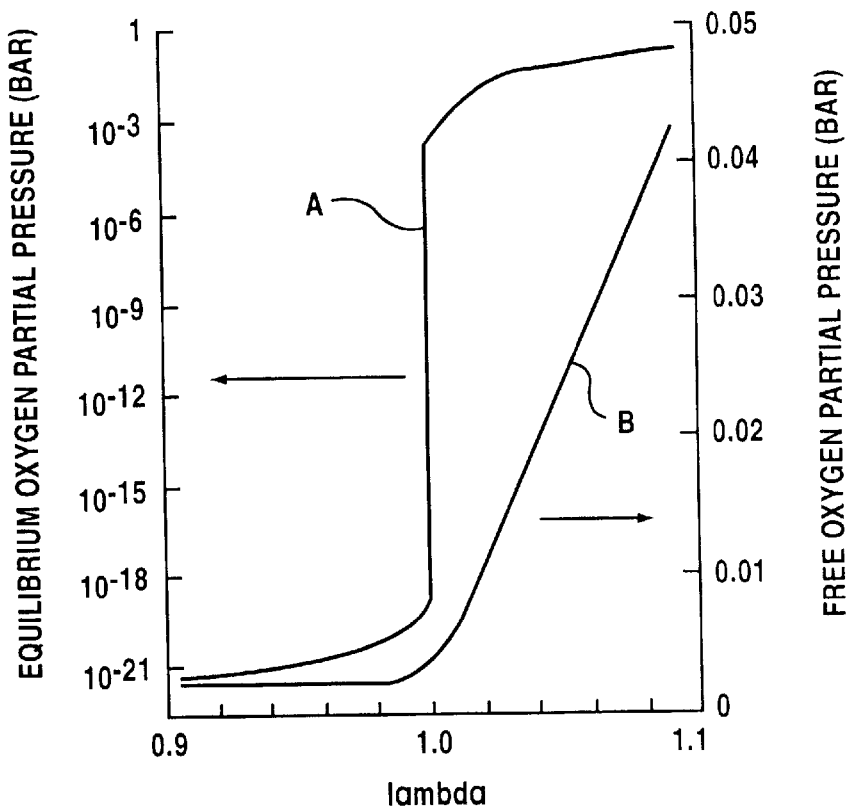
FIG. 3 is a diagram representing a first characteristic curve of an equilibrium oxygen partial pressure of the exhaust gas as a function of an air factor.

Referring now to the figures of the drawings in detail and first, particularly, to FIG. 1 thereof, there is seen a diagrammatic structure of an exhaust-gas probe 8 which has a substrate 1 made of aluminum oxide. A heating element 2, which heats the exhaust-gas probe 8 to a predetermined operating temperature of between 800° C. and 900° C., is disposed in the substrate 1. A measuring electrode 3, which is formed of platinum, is formed on an upper surface of the substrate 1. A metal oxide layer 4, which is formed of strontium titanate ($SrTiO_3$), is applied over the measuring electrode 3. The exhaust-gas probe 8 represents an oxygen sensor. In order to measure the resistance of the metal oxide layer 4, a voltage is applied to connection points 11, 12 of the measuring electrode 3, and the resistance is calculated from the current.

FIG. 2 shows a configuration for investigating the functional capability of a catalytic converter 7. An exhaust pipe 6 is connected to an internal combustion engine 5 and to the catalytic converter 7 and is continued at an outlet of the catalytic converter 7. The exhaust-gas probe 8 is fitted either in the catalytic converter 7 or downstream of the catalytic converter 7 in the exhaust pipe 6 and is connected through measuring lines 13 to a computer unit 9. The computer unit 9 has access over a data line to a memory 14 which stores characteristic curves for the resistance of the exhaust-gas probe 8 as a function of an air factor or value λ upon injection and a conversion efficiency η of the catalytic converter 7. In addition, a control line 15 is connected to the computer unit 9 and leads to an injection system 10 of the internal combustion engine 5.

FIG. 3 shows a diagram which represents a first characteristic curve A that illustrates the equilibrium oxygen partial pressure of the exhaust gas as a function of the air factor λ. The pressure is specified in bar for the first characteristic curve A. In addition, a second characteristic curve B which is shown in the diagram describes the free oxygen partial pressure of the exhaust gas as a function of the air factor λ. The pressure for the second characteristic curve B is likewise specified in bar.

An equilibrium oxygen partial pressure is established in the exhaust gas downstream of the catalytic converter 7 if the conversion efficiency of the catalytic converter 7 is high and therefore the functional capability of the catalytic converter 7 is as it should be. A free oxygen partial pressure in the exhaust gas is converted into an equilibrium oxygen partial pressure by the catalytic effect of the catalytic converter 7, so that with a properly functioning catalytic converter 7, a characteristic curve corresponding to the first characteristic curve A as a function of the air factor λ is measured in or downstream of the catalytic converter 7.

If the catalytic converter 7 has zero conversion efficiency, a free oxygen partial pressure results in the exhaust gas in or downstream of the catalytic converter 7, so that the second characteristic curve B is measured in or downstream of the catalytic converter 7 as a function of the air factor ratio λ. In the case of a partially functioning catalytic converter 7, a characteristic curve is established which lies between the first characteristic curve A and the second characteristic curve B.

Figure 4:
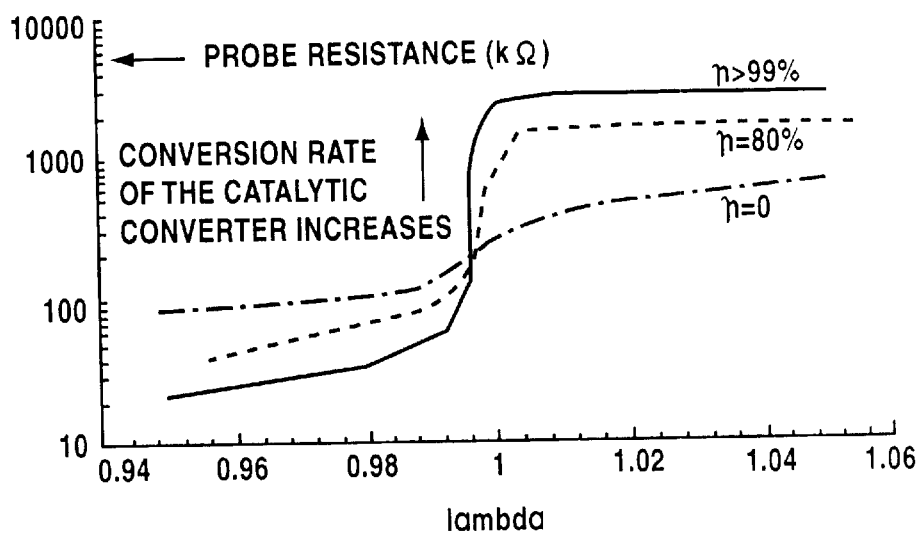
FIG. 4 is a diagram representing characteristic curves for resistance of the exhaust-gas probe as a function of the air factor and a conversion efficiency of the catalytic converter.

FIG. 4 shows a diagram which indicates characteristic curves for the resistance of the exhaust-gas probe 8 as a function of the air factor λ and the conversion efficiency η of the catalytic converter 7. The conversion efficiency η is a measure of the catalytic activity and, for example, is defined as follows:

$\eta = (HC_{up} - HC_{down})/HC_{up}$, wherein $HC_{up}$ indicates a concentration of hydrocarbon compounds upstream of the catalytic converter 7, and $HC_{down}$ indicates a concentration of hydrocarbon compounds downstream of the catalytic converter 7.

In this example, the conversion efficiency of the catalytic converter 7 is specified explicitly for hydrocarbon compounds, and it is also possible to consider the conversion efficiency for other compounds, for example carbon monoxide (CO) or nitrogen oxides (NOx). The formula for the conversion efficiency of the catalytic converter 7, with reference to carbon monoxide and nitrogen oxide, is provided in similar fashion to the formula for the conversion efficiency of hydrocarbon compounds.

The resistance of the exhaust-gas probe 8 is plotted on the vertical axis with a logarithmic scale, and the air factor λ is plotted on the horizontal axis. If the conversion efficiency of the catalytic converter is equal to 0, then the resistance of the exhaust-gas probe 8 increases from a value of about 100 kOhm for an air factor of less than 1 to about 300 kOhm for an air factor λ of greater than 1. If the conversion efficiency η of the catalytic converter 7 is greater than 99%, then the resistance of the exhaust-gas probe 8 for an air factor λ<1 has a value of about 25 kOhm and increases for an air factor λ>1 to a value of 3000 kOhm.

If the conversion efficiency lies between the values 0 and 99%, then characteristic curves result which lie between the two specified characteristic curves. FIG. 4 clearly shows that the conversion efficiency of the catalytic converter 7 has a great influence on the resistance of the metal oxide layer 4 of the exhaust-gas probe 8, which has minimal catalytic activity. The catalytic action of the metal oxide layer 4 on the exhaust gas is determined by the conversion efficiency ηm, wherein the conversion efficiency ηm is defined as follows:

$\eta m = (HC_{without} - HC_{with})/HC_{without}$, wherein $HC_{without}$ indicates the concentration of hydrocarbon compounds without the effect of the catalytic metal oxide layer 4, and $HC_{with}$ indicates the concentration of hydrocarbon compounds under the effect of the catalytic metal oxide layer 4. Further metal oxide layers with low catalytic activity are, for example: cerium oxide ($CeO_2$), gallium oxide ($Ga_2O_3$) and titanium oxide ($TiO_2$).

In this example, the conversion efficiency of the active metal oxide layer 4 is specified explicitly for hydrocarbon compounds, with it also being possible to consider the conversion efficiency for other compounds, for example carbon monoxide (CO) or nitrogen oxides (NOx). The formula for the conversion efficiency of the active metal oxide layer 4, with reference to carbon monoxide and nitrogen oxide, is provided in a similar manner to the formula for the conversion efficiency of hydrocarbon compounds.

The resistance R of the metal oxide layer 4 is inversely proportional to the conductivity σ. The conductivity σ has the following dependence:

$\sigma(T) = \sigma_0 \cdot Exp(-E/kT) \cdot f(p_O)$, wherein $\sigma_0$ indicates a conductivity constant, E indicates an activation energy, k indicates Boltzmann's constant, T indicates the absolute temperature, and $f(p_O)$ indicates a function of the oxygen partial pressure in the environment of the metal oxide layer 4.

In the case of an n-conducting metal oxide, for example, the electrical resistance increases with increasing oxygen partial pressure. In rich exhaust-gas mixtures (λ<1) the resistance decreases with increasing conversion efficiency of the catalytic converter, because the oxygen partial pressure in the exhaust gas decreases by orders of magnitude. In lean exhaust-gas mixtures (λ>1), cross sensitivity leads to an increase in resistance with increasing conversion efficiency of the catalytic converter.

The function of the configuration according to the invention is explained in more detail with reference to FIG. 2 and FIG. 4. The computer unit 9 measures the resistance of the n-conducting metal oxide layer 4 of the exhaust-gas probe 8, which is disposed downstream of the catalytic converter 7 in the exhaust pipe 6. In this case, the resistance values of the exhaust-gas probe 8 can be evaluated in various ways.

One way of evaluating the resistance of the exhaust-gas probe 8 is by comparing the resistance measured by the computer unit 9 with characteristic curves which are stored in the memory 14 and specify the resistance of the exhaust-gas probe 8 as a function of the air factor λ and as a function of the conversion efficiency of the catalytic converter 7, in accordance with FIG. 4. The computer unit 9 assigns a measured resistance to a stored characteristic curve and thereby determines the conversion efficiency of the catalytic converter 7.

According to FIG. 4, for a λ value of greater than 1, a resistance of 3000 kOhm is an indication that the conversion efficiency η is greater than 99%. If, however, for a λ value of greater than 1, the resistance has a value of 200 kOhm, then this value corresponds to the resistance characteristic curve for the conversion efficiency η=0, i.e. the catalytic converter 7 has zero conversion efficiency.

The exhaust-gas probe 8 exhibits jumps in resistance, which can be seen upon comparison with FIG. 4 for predetermined λ control, with which an air-fuel ratio is alternately set up with a value λ<1 and a value λ>1 upstream of the internal combustion engine 5. The size of the jumps in resistance increases as the conversion efficiency of the catalytic converter 7 improves. The amplitude of the fluctuation in the resistance of the exhaust-gas probe 8 is in direct relation with the conversion efficiency of the catalytic converter.

A further worry of investigating the conversion efficiency is based on comparing the jumps in resistance for the change from λ<1 to λ>1 with a predetermined resistance threshold of, for example, 600 kOhm, and registering a catalytic converter 7 as being functional if the jumps in resistance are greater than the predetermined resistance threshold.

We claim:

1. A method for testing the functional capability of a catalytic converter of an internal combustion engine, which comprises:

placing an oxygen sensor in a catalytic converter;

providing the oxygen sensor with a layer having at most little catalytic effect on exhaust gas;

measuring resistance of the layer;

determining a reference value using values or characteristic curves for the resistance of the layer that are a function of an air factor and of a conversion rate of the catalytic converter;

comparing the measured resistance with the reference value to reach a result; and evaluating the result of the comparison as a measure of a conversion efficiency of the catalytic converter.

2. The method according to claim 1, which comprises measuring the resistance of the layer for an air factor of less than one and for an air-fuel ratio of greater than one to determine a difference, and using the difference between the measured resistances as a measure of the conversion efficiency of the catalytic converter.

3. The method according to claim 2, which comprises deciding that the catalytic converter is defective if the difference between the resistance values is greater than a limit value.

4. The method according to claim 1, which comprises forming the layer as a metal oxide layer.

5. A method for testing the functional capability of a catalytic converter of an internal combustion engine, which comprises:

placing an oxygen sensor in an exhaust pipe downstream of a catalytic converter;

providing the oxygen sensor with a layer having at most little catalytic effect on exhaust gas;

measuring resistance of the layer;

determining a reference value using values or characteristic curves for the resistance of the layer that are a function of an air factor and of a conversion rate of the catalytic converter;

comparing the measured resistance with the reference value to reach a result; and evaluating the result of the comparison as a measure of a conversion efficiency of the catalytic converter.

6. The method according to claim 5, which comprises measuring the resistance of the layer for an air factor of less than one and for an air-fuel ratio of greater than one to determine a difference, and using the difference between the measured resistances as a measure of the conversion efficiency of the catalytic converter.

7. The method according to claim 6, which comprises deciding that the catalytic converter is defective if the difference between the resistance values is greater than a limit value.

8. The method according to claim 5, which comprises forming the layer as a metal oxide layer.

* * * * *